United States Patent
Massonnat et al.

(10) Patent No.: US 12,298,465 B2
(45) Date of Patent: May 13, 2025

(54) METHOD FOR DETERMINATION OF REAL SUBSOIL COMPOSITION

(71) Applicant: TotalEnergies OneTech, Courbevoie (FR)

(72) Inventors: Gérard Massonnat, Pau (FR); David Ledez, Pau (FR); Jean-Paul Rolando, Pau (FR)

(73) Assignee: TotalEnergies OneTech, Courbevoie (FR)

( * ) Notice: Subject to any disclaimer, the term of this patent is extended or adjusted under 35 U.S.C. 154(b) by 763 days.

(21) Appl. No.: 17/253,556

(22) PCT Filed: Jun. 20, 2018

(86) PCT No.: PCT/IB2018/001633
§ 371 (c)(1),
(2) Date: Dec. 17, 2020

(87) PCT Pub. No.: WO2019/243865
PCT Pub. Date: Dec. 26, 2019

(65) Prior Publication Data
US 2021/0270997 A1    Sep. 2, 2021

(51) Int. Cl.
*G06F 30/20*     (2020.01)
*G01N 33/24*     (2006.01)
*G01V 9/00*      (2006.01)
*G01V 20/00*     (2024.01)

(52) U.S. Cl.
CPC ............. *G01V 9/007* (2013.01); *G01N 33/24* (2013.01); *G01V 20/00* (2024.01)

(58) Field of Classification Search
CPC ....... G01N 33/24; G01V 9/007; G01V 99/005
See application file for complete search history.

(56) References Cited

U.S. PATENT DOCUMENTS

| | | | |
|---|---|---|---|
| 10,422,923 B2 * | 9/2019 | Hugot | G01V 1/301 |
| 2010/0332205 A1 | 12/2010 | Tillier et al. | |
| 2011/0298802 A1 * | 12/2011 | Whitaker | G06T 17/20 345/423 |
| 2011/0310101 A1 | 12/2011 | Prange et al. | |
| 2013/0262063 A1 * | 10/2013 | Massonat | G06F 30/20 703/6 |

(Continued)

FOREIGN PATENT DOCUMENTS

WO    2012/072923 A2    6/2012

OTHER PUBLICATIONS

De Oliveira Miranda, Antonio Carlos, et al. "Finite element mesh generation for subsurface simulation models." Engineering with Computers 31 (2015): 305-324.*

(Continued)

*Primary Examiner* — Nithya J. Moll
(74) *Attorney, Agent, or Firm* — Seed IP Law Group LLP

(57) ABSTRACT

The present invention relates to a method for determination of real subsoil composition or structure characterized in that the method comprises: —reception of unmeshed model representing the real subsoil; —determination of a sediment trajectory in said model; —based on the sediment trajectory, determination of at least one parametric surface describing a sediment formation in said model; —based on the least one parametric surface, meshing the sediment formation in said model.

7 Claims, 13 Drawing Sheets

(56) References Cited

U.S. PATENT DOCUMENTS

2015/0212231 A1* 7/2015 Borouchaki ............ G06T 17/05
703/10

OTHER PUBLICATIONS

Jacquemyn et al., "Geologic Modelling Using Parametric NURBS Surfaces," ECMOR XV—15$^{th}$ European Conference on the Mathematics of Oil Recovery, Aug. 29-Sep. 1, 2016, Amsterdam, Netherlands, 10 pages.

* cited by examiner

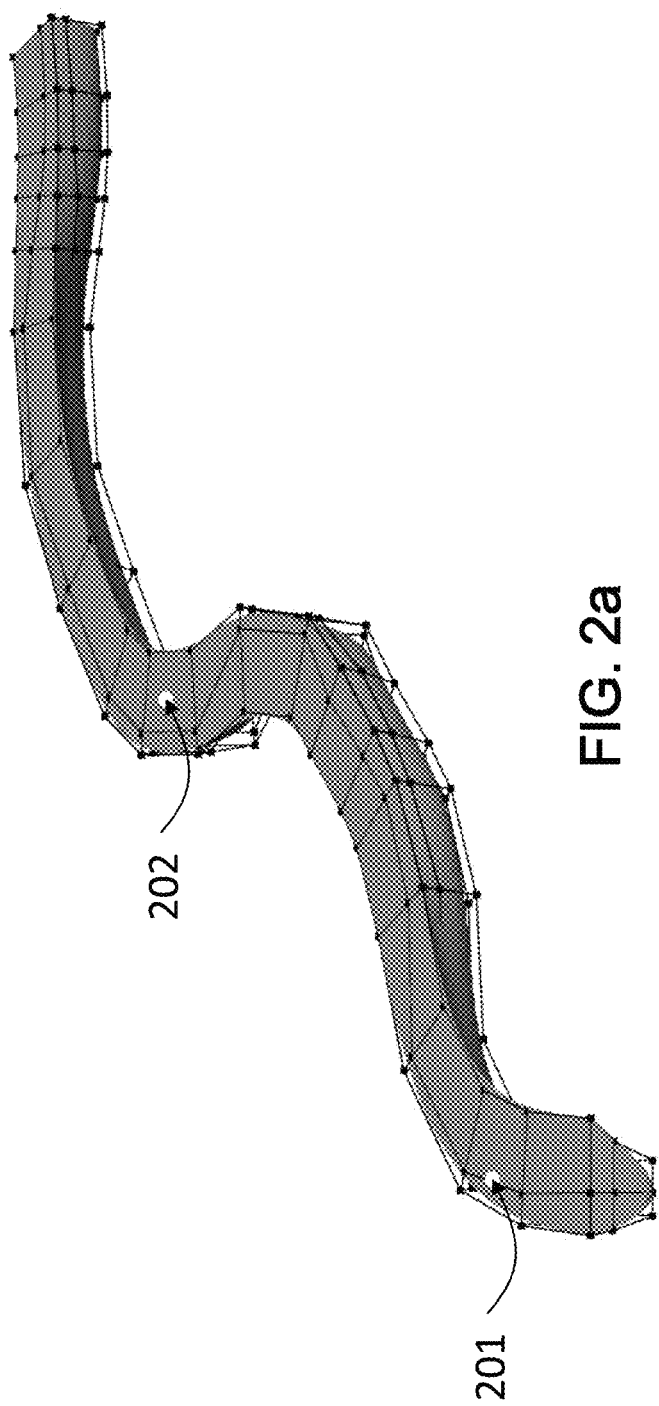

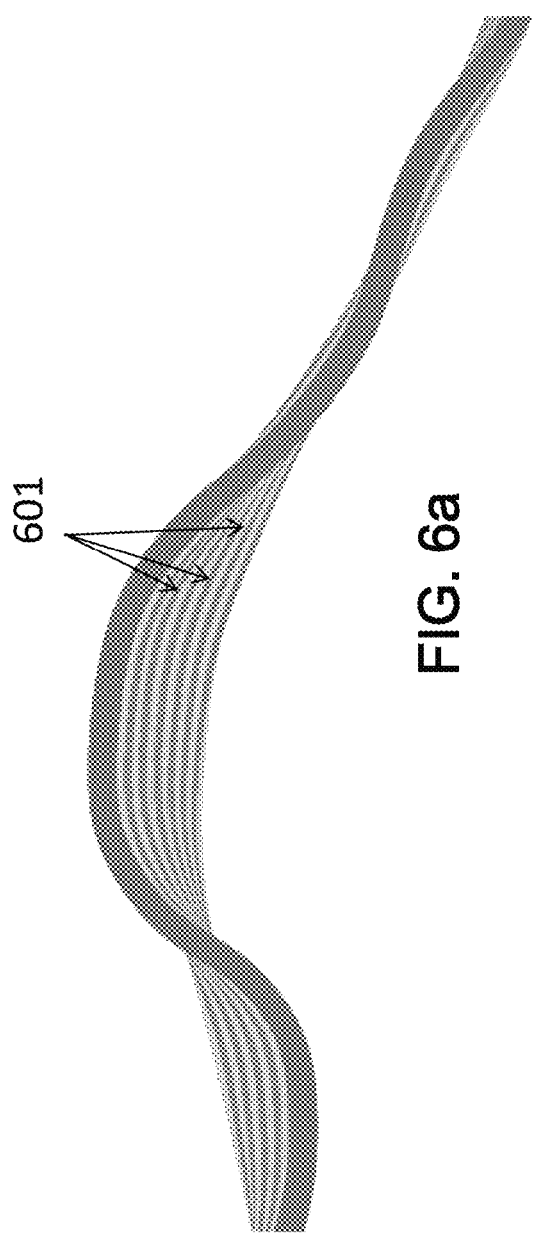
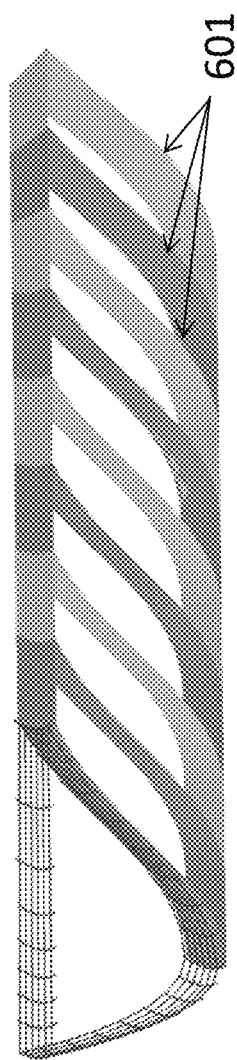
FIG. 6a
FIG. 6b

METHOD FOR DETERMINATION OF REAL SUBSOIL COMPOSITION

BACKGROUND OF THE INVENTION

The present invention relates to determination of subsoil compositions/property, especially for the use in the hydrocarbon industries.

The approaches described in this section could be pursued, but are not necessarily approaches that have been previously conceived or pursued. Therefore, unless otherwise indicated herein, the approaches described in this section are not prior art to the claims in this application and are not admitted to be prior art by inclusion in this section. Furthermore, all embodiments are not necessarily intended to solve all or even any of the problems brought forward in this section.

In the past, when a subsoil composition should be determined, a same paradigm is used: "the model used for said determination should be meshed before any modeling".

Indeed, for any modeling methods, the meshing is mandatory.

Nevertheless, it is well known that this meshing prior to any modeling has several drawbacks as the size of the meshes, the orientation of the meshes, the number of the meshes induce bias in the modeling.

For instance, this meshing prior to any modeling cannot take into account the sedimentary bodies of the subsoil which will be identified during the modeling phase.

It is noted that the accurate determination of the subsoil composition and structure is a key feature for determining hydrocarbon reservoirs and enabling a proper industrial extraction of hydrocarbons.

In addition, when working with pre-meshed model, it may be difficult to accurately satisfy the well constraints (i.e. log data) as the log data may be transformed with blocking methods to adapt the precision of the log data to the dimension of the cells.

Furthermore, in prior art methods, it may be difficult to associate the cells with facies or geophysical property as the dimension of the cell does not allow a proper identification of their respective position in the geological formations.

SUMMARY OF THE INVENTION

The invention relates to a method for determination of real subsoil composition characterized in that the method comprises:
  reception of unmeshed model representing the real subsoil;
  determination of a fluvial trajectory in said model;
  based on the fluvial trajectory, determination of at least one parametric surface describing a fluvial formation in said model;
  based on the least one parametric surface, meshing the fluvial formation in said model.

Thanks to said method, it is possible to adequately mesh part of the model and thus to effectively run method(s) to determine real subsoil composition. The meshing is far more accurate than a priori methods of the prior art.

Therefore, a last step of the method may be to determine real subsoil composition based on the meshed formation or/and output said result for future use in geophysical tools (e.g. prevision of hydrocarbon production, determination of a correct location of a well to be drilled, estimation of the reservoir capacity).

In addition, the determination of the at least one parametric surface may be based on NURBS curve or NURBS surface or NURBS volume.

In the followings, it is possible to use any "B-splines" or "splines" instead of "NURBS".

Relating to NURBS, the document "An Introduction to NURBS—ISBN: 9781558606692" that is included by reference describes any concepts and algorithms needed to manipulate NURBS.

Optionally, the determination of the fluvial trajectory may be based on a stochastic process.

Furthermore, the meshing of the fluvial zone may be based on a method in a group comprising Quadtree meshing method, the Octree meshing method, Front method, Delaunay method, Prograding grid, divergent grid, and aggrading grid.

The method may further comprise:
  meshing of at least a part of the model that is not a determined formation.

In addition, the method may further comprise:
  determining at least one associated surface function of the at least one parametric surface, said associated surface describing a associated geological formation associated with the fluvial formation.

The invention relates to a method for determination of real subsoil composition characterized in that the method comprises:
  reception of a model representing the real subsoil, said model comprising at least one parametric surface describing a geological formation in said model;
  receiving a geological constraint to be satisfied by said geological formation;
  determining if the constraint is satisfied by the said geological formation;
  if the constraint is not satisfied by the said geological formation, distortion of the parametric surface so that the constraint is satisfied by the said geological formation.

Thanks to said method, it is possible to create model that easily satisfy the constraints provided. This method is far better than prior art methods as the distortion is performed on surfaces (with is very simple by known algorithms) while prior art methods deal with cells inclusion/exclusion, far more complex.

Therefore, a last step of the method may be to determine real subsoil composition based on the distorted formation or/and output said result for future use in geophysical tools (e.g. prevision of hydrocarbon production, determination of a correct location of a well to be drilled, estimation of the reservoir capacity).

The parametric surface may be based on NURBS curve or NURBS surface or NURBS volume.

In addition, the distortion of the parametric surface may comprise a prior step of determining a point in said surface minimizing a distance between a distance of said point and a position of said constraint.

The geological constraints may be based on a constraint in a group comprising a data log constraint and a seismic constraint.

Optionally, the constraint may be satisfied when a position of said constraint is inside the geological formation.

The invention relates to a method for determination of real subsoil composition characterized in that the method comprises:
  receiving a model representing the real subsoil, said model comprising at least one parametric volume describing a geological formation in said model, said volume having a plurality of cells;

for each cell in the plurality of cells, determining a quality index ($QI_c$) function of a respective position of the cell in the geological formation;

receiving a set of facies, each facies in said set being associated with a proportion and a quality index ordering in said formation;

associating a facies to each cell, said association comprising:
/a/ selecting a cell with a lowest quality index within cells in the plurality of cells having no facies associated to;
/b/ associating, to said cell, a facies with a lowest Quality index ordering within facies of the set of facies for which the respective proportion is not reached in the formation;
/c/ reiterating steps /a/ to /c/ until all cells in the plurality of cells are associated with a facies.

Thanks to said method, it is possible to easily associate facies to cells.

Therefore, a last step of the method may be to determine real subsoil composition based on the distorted formation or/and output said result for future use in geophysical tools (e.g. prevision of hydrocarbon production, determination of a correct location of a well to be drilled, estimation of the reservoir capacity).

The invention relates to a method for determination of real subsoil composition characterized in that the method comprises:

receiving a model representing the real subsoil, said model comprising at least one parametric volume describing a geological formation in said model, said volume having a plurality of cells, the number of cells in the plurality of cells being M;

for each cell in the plurality of cells, determining a quality index ($QI_c$) function of a respective position of the cell in the geological formation;

receiving a property distribution;

determining M random draws of property value based on the property distribution, said random draws having a respective property order so that, for any first random draw of a first property value and with a first property order and for any second random draw of a second property value and with a second property order, if the second property value is greater than the first property value, then the second property order is strictly greater than the first property order;

associating a property value to each cell, said association comprising:
/a/ selecting a cell with a lowest quality index within cells in the plurality of cells having no property associated to;
/b/ associating, to said cell, a random draw of property value in the M random draws with a lowest property order within random draws that have not been associated yet with a cell;
/c/ reiterating steps /a/ to /c/ until all cells in the plurality of cells are associated with a property.

Thanks to said method, it is possible to easily associate property to cells.

Therefore, a last step of the method may be to determine real subsoil composition based on the distorted formation or/and output said result for future use in geophysical tools (e.g. prevision of hydrocarbon production, determination of a correct location of a well to be drilled, estimation of the reservoir capacity).

Another aspect relates to a computer program product comprising a computer-readable medium, having thereon a computer program comprising program instructions. The computer program is loadable into a data-processing unit and adapted to cause the data-processing unit to carry out the method(s) described above when the computer program is run by the data-processing unit.

Other features and advantages of the method and apparatus disclosed herein will become apparent from the following description of non-limiting embodiments, with reference to the appended drawings.

BRIEF DESCRIPTION OF THE DRAWINGS

The present invention is illustrated by way of example, and not by way of limitations, in the figures of the accompanying drawings, in which like reference numerals refer to similar elements and in which:

FIGS. 2a and 2b are respectively a 3D view of a fluvial geological formation and a top view of a fluvial geological formation;

FIGS. 6a and 6b are respectively a top view of associated geological formations and 3D view said associated geological formations;

DESCRIPTION OF PREFERRED EMBODIMENTS

In the following description, fluvial geological formations are described to exemplify the invention but it applies to any possible geological formations (e.g. lobes, turbiditic systems, etc.)

Therefore, in the following, "fluvial trajectory" may be replaced by "sediment trajectory" without significant modification.

Figure 1:
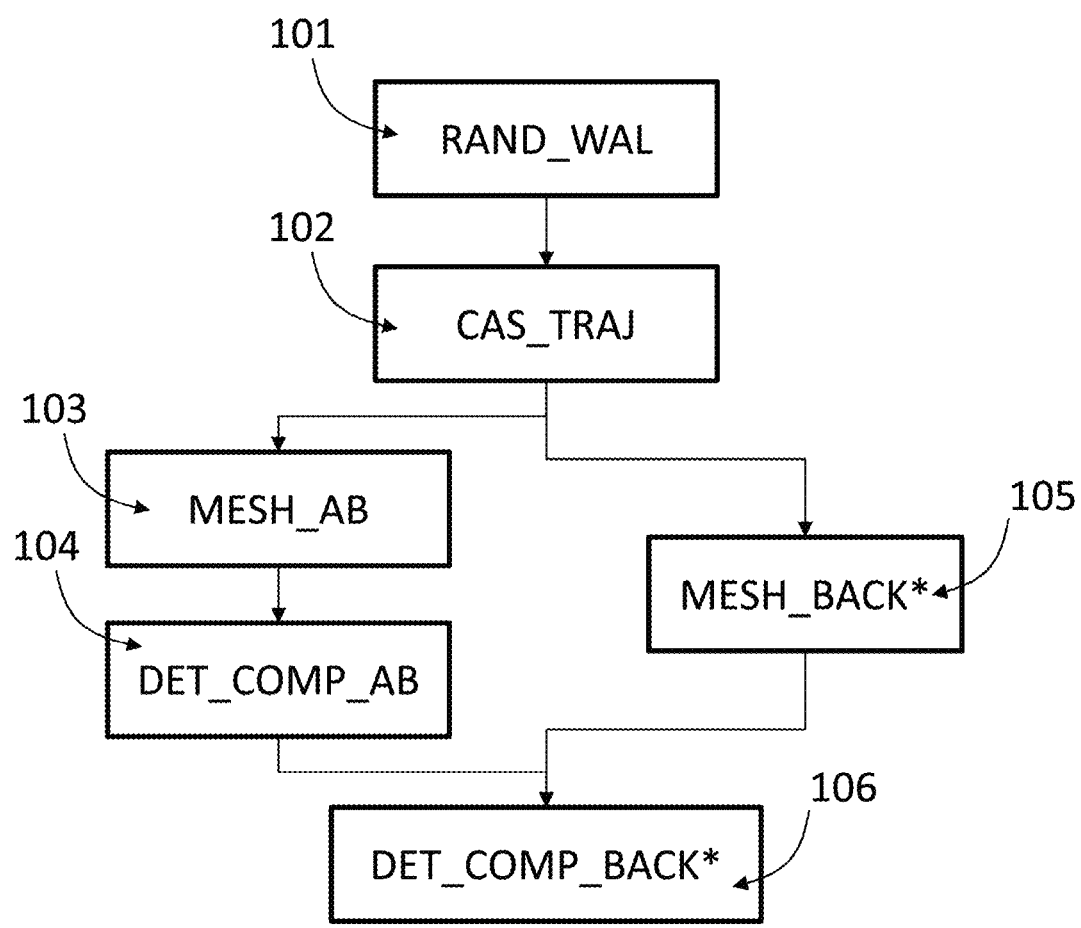
FIG. 1 is a general workflow of a possible embodiment of the invention.

FIG. 1 is a chart describing a possible process of the invention.

In this chart, the manipulated model is possibly a parametric model of the subsoil. A parametric model $M_p(u,v,t)$ of the subsoil is a transformation of a 3D model $M(x,y,z)$ of the subsoil.

A 3D model $M(x,y,z)$ of a real subsoil describes the subsoil according to its real geographical coordinates $(x,y,z)$ (i.e. at the present time).

A parametric model $M_p(u,v,t)$ of said subsoil describes the state of the subsoil at a geological time t: each layer represents the state of the subsoil at the time t where the sedimentation occurs. One may say that the parametric model $M_p(u,v,t)$ restore the horizontal layer for a given sedimentation/geological time t.

In the manipulated model, it is possible to simulate the geological formation of a fluvial zone. Said geological formation determination of a fluvial zone may comprise, as described in WO 2012/072923, the displacement of particles (step 101) in the manipulated model by superimposing:
 a deterministic term defined on the basis of observation data for the fluvial zone to be determined, and
 a stochastic term parametrized at least by the observation data.

It is possible to take into account both the fluid flow of the particles in the zone, and to introduce a probabilistic perturbation.

When one speaks of superposition of two terms, it will be understood that the simulated displacement is composed from the sum of the deterministic term and of the stochastic term.

The stochastic term can comprise the superposition of a meandriform term and of a random perturbation. So doing, the modeling of the channel is rendered more realistic.

The meandriform term can comprise a superposition of at least one trigonometric function. Such a representation is realistic for a meandriform term, and easily parametrizable.

The observation data can comprise at least one of the following types of data:
 a gradient of flow speed in the zone,
 geometric parameters of the zone,
 data arising from drilling,
 data arising from imaging, especially seismic imaging.

It is noted that the model does not need to be meshed up to this point. A parametric description of the trajectory may be easily determined in the model.

Once the respective trajectory 201 (see FIGS. 2a, 2b) of geological formation(s) of a fluvial zone is/are determined (for the sake of the understanding, the singular is used in the following, considering that only one trajectory 201 is determined, but it is apparent that the plural may also be used), it is possible to determine surface(s) (step 102) that represent the extend of the determined geological formation, the trajectory being inside said extends. This extends may represent the bed of a river/torrent/etc. or any geological formation of the fluvial zone (see element 202, FIGS. 2a, 2b).

To describe these surfaces, it is possible to use NURBS (or non-uniform Rational B-Splines).

Non-uniform rational basis spline (NURBS) is a mathematical model used in computer graphics for generating and representing curves and surfaces. It offers great flexibility and precision for handling both analytic (surfaces defined by common mathematical formulae) and modeled shapes.

Therefore there is no need to identify the bed of said formations by identifying the meshes/cells of the meshed model that are inside the bed: a parametric description of said formations enables a far better meshing performed at a later stage fitting the NURBS surfaces.

Figure 3A:
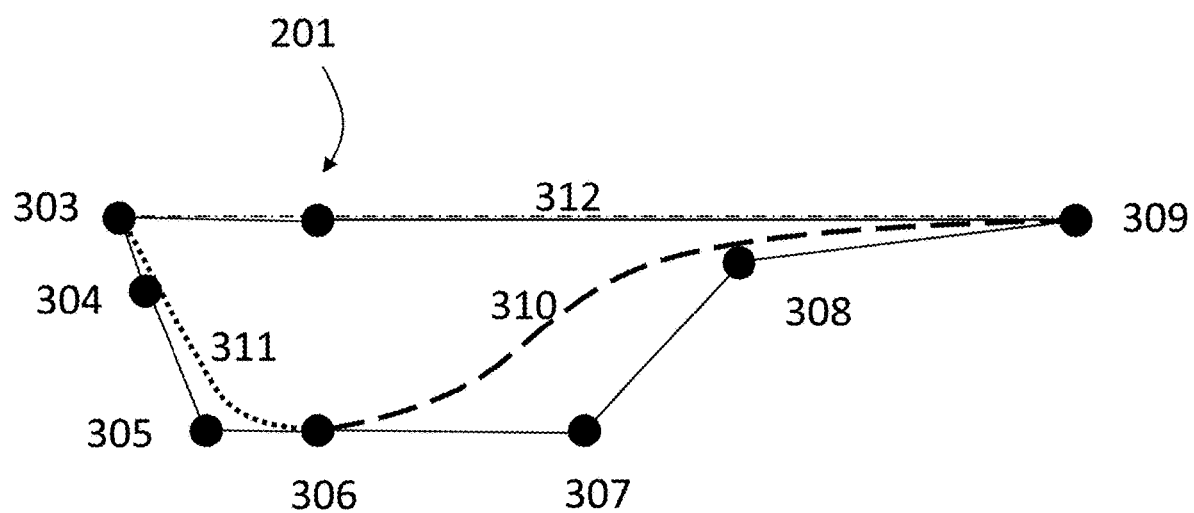
FIG. 3a is a representation of surfaces/sides determination of a fluvial geological formation with NURBS surfaces.

For instance, in FIG. 3a, a side view of the model is shown, the trajectory 201 being perpendicular to said view. In said figure, trajectory 201 is represented as a single point. When referring to "point 201", one means the point corresponding to the intersection between the view plan of figure and the trajectory 201.

To represent the extend of the determined geological formation, it is possible to represent the shape of bed by a plurality of NURBS 310, 311 and 312, ensuring that the contacts of these NURBS satisfy some parametric continuity (for instance $C^0$, $C^1$ and/or $C^2$) and/or some geometric continuity (for instance $G^0$, $G^1$ and/or $G^2$).

Figure 2B:
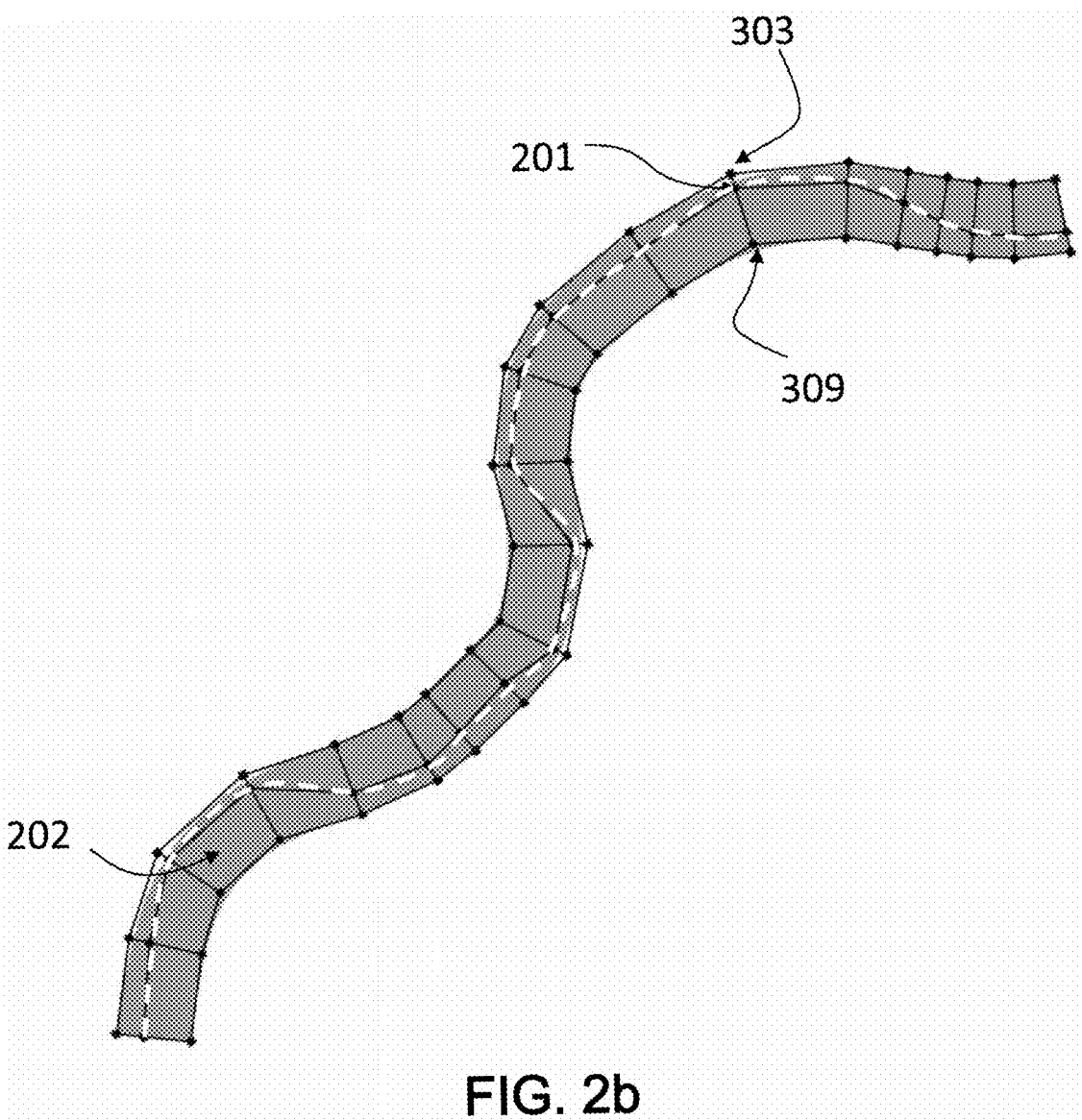

In the example of FIG. 3a, point 303 and 309 may be defined such that 303, 201 and 309 are aligned, the respective distance between 303-201 and 201-309 may be function of the local curvature of the trajectory 201 (see FIG. 2b).

In said example, point 303 represents a point on the convex side of the curvature of the trajectory 201; point 309 represents a point on the concave side of the curvature of the trajectory 201. Thus, it is possible to compute the distances 303-201 and 201-309 as a function of the local curvature of the trajectory 201 and such that the distance 303-201 is lower than distance 309-201.

Point 306 may be determined such that the line (306;201) is perpendicular to the line (303;309) and such that the distance 306-201 is either a predetermined value or function of the local curvature or function of the distance 303-309.

In addition, once the positions of points 306, 303 and 309 are determined, it is possible to determine a plurality of set of points 304, 305 307 and 308. These points may have a location function of the positions of points 306, 303 and 309 and/or the curvature of trajectory 201.

Points 303, 304, 305, 306 may define a first NURBS 311.
Points 309, 308, 307, 306 may define a second NURBS 310.

A third NURBS 312 may be defined to close the shape of the bed.

NURBS curves may be determined thanks to the Cox-de Boor's Algorithm.

This process is described in regard of a side view of the trajectory (perpendicular to said trajectory) but can be reiterated for a plurality of different side views of the trajectory (see FIG. 2b for instance). Then, NURBS surfaces may be defined thanks to the NURBS curves (or thanks to points that have been used to define the NURBS curves).

Figure 3B:
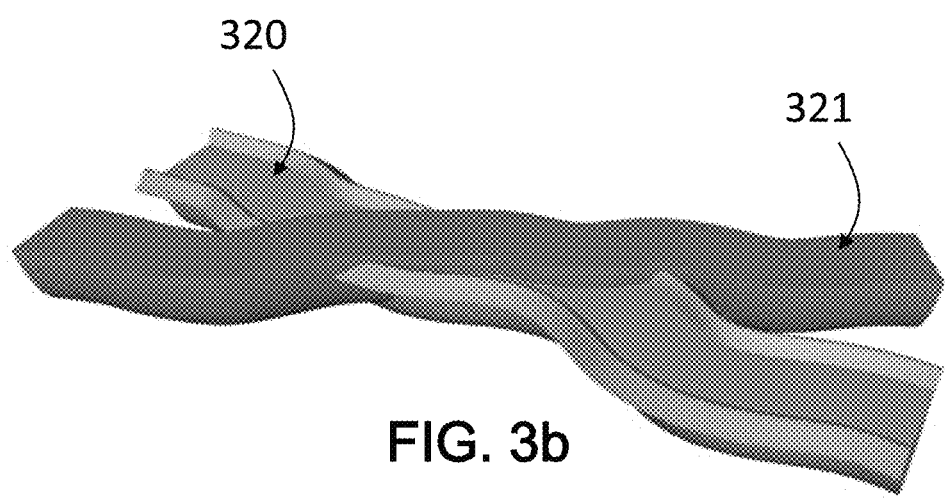
FIGS. 3b and 3c are 3D view of interconnected fluvial geological formations.
Figure 3C:
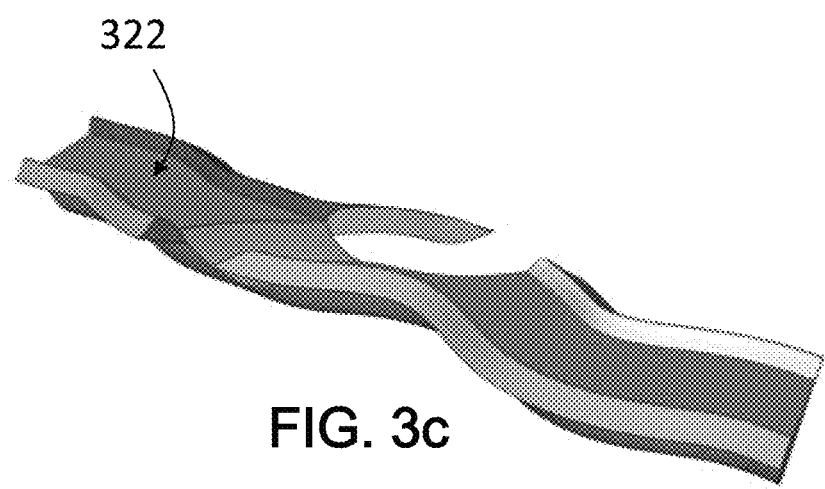

The use of the NURBS surfaces is very effective as it is very simple to "subtract" volumes of determined geological formations. For instance, referring to FIG. 3b, if two geological formations 320 and 321 are determined and if their respective volumes intersect each other, available NURBS intersection algorithms provide accurate and effective method to subtract the volume of formation 321 to formation 320 (representing the replacement of the formation 320 by formation 321 due to hydrodynamic/fluvial erosion) to create the new volume 322 (FIG. 3c). Algorithms based on cells/meshes (i.e. identifying cells that are in both formations) are not as accurate and effective as the NURBS algorithms.

Figure 4A:
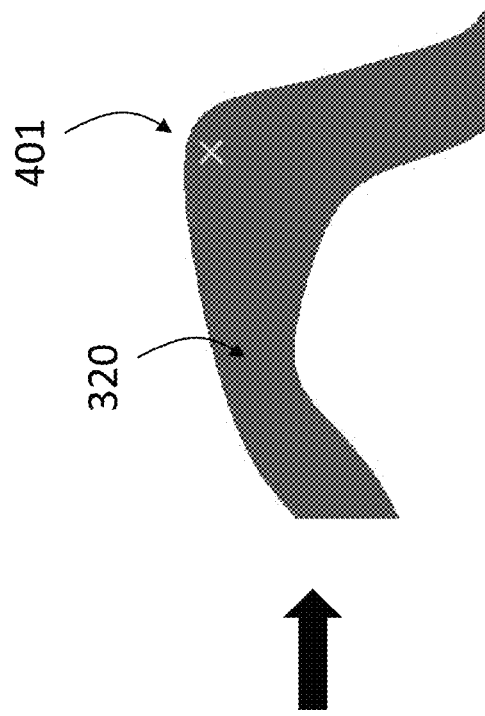
FIG. 4a is a top view of a distortion of a representation of a geological formation to satisfy a well constraint (horizontal distortion)
Figure 4A:
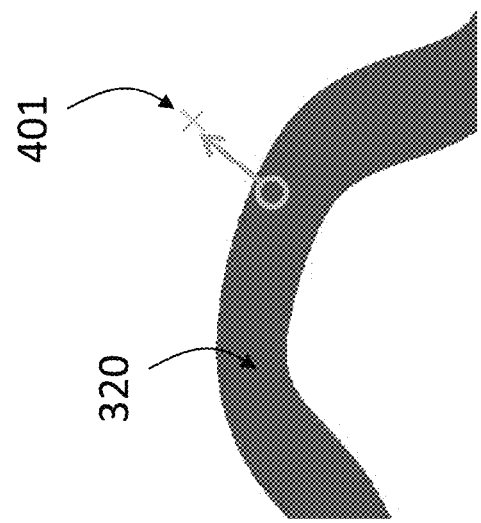

In addition, if the model has some constraints (e.g. a seismic or geological indication that a formation is present at a given location), it is possible to distort the closest NURBS 320 to ensure that this constraint 401 (see FIG. 4a, which is a top view of the model) is satisfied. The distortion methods for NURBS surfaces are well available. Therefore it is possible to satisfy all constraints of the model.

Figure 4B:
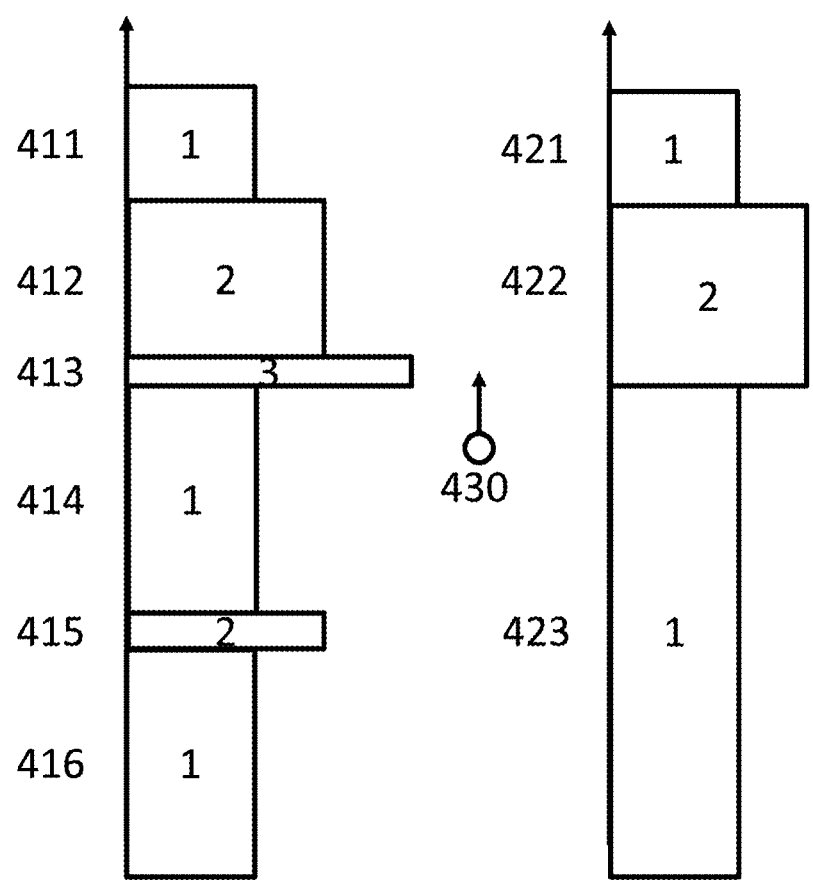
FIG. 4b is a representation of well data and provide indication on distortion of a geological formation to satisfy a well constraint (vertical distortion)

It is also possible to distort the formation vertically to match the constraints but within a given distance/zone. For instance, if one may want to satisfy the well-data (see FIG. 4b) represented by layer 411-416, it is possible to use directly the logs without applying a blocking method (which was mandatory in the method of the prior art, i.e. the reduction to coarser layers 421-423). Thanks to said method, if it is known that a fluvial formation is in the layer 413 and that the closest formation is at position 430, it is easy to distort the NURBS to satisfy the constraints. With a blocking method, this constraint may not be satisfied as the layer 413 may disappear.

Once the formations are determined thanks to the NURBS surfaces, it is possible to mesh the formations (step 103 of FIG. 1) according to the formations surfaces definition.

Figure 5:
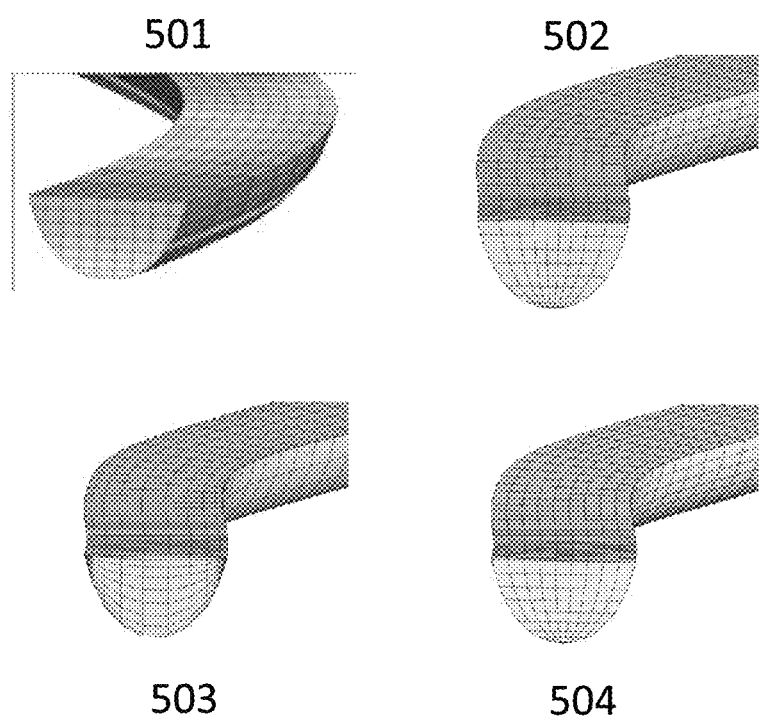
FIG. 5 provides examples regarding the meshing of geological formations.

A plurality of meshing is possible as described in FIG. 5. For instance, meshes 501, 502, 503 or 104 are possible. Well known methods such as the Quadtree meshing method, the Octree meshing method, Front method, Delaunay method, Prograding grid, divergent grid, aggrading grid, etc. are possible.

It is possible to understand that the meshing performed a posteriori (i.e. after the determination of the formation shapes) is far better (i.e. fits the shape of the geological bodies) than a meshing performed a priori (i.e. before any shape determination of geological formation).

Figure 6C:
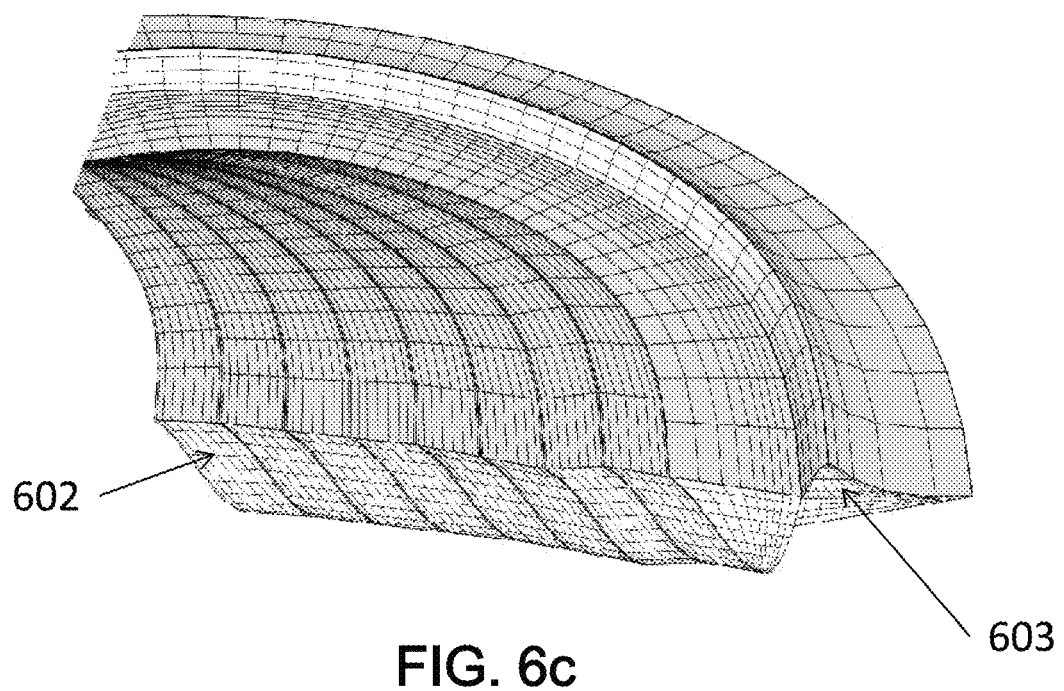
FIG. 6c provides examples regarding the meshing of associated geological formations.

In addition, based on the first geological formations determined, it is possible to create related formations such as lobes (i.e. at an end of the fluvial formation), bar, point bar (see FIGS. 6a and 6b, the number of internal surfaces 601 or the distance between surfaces 601 may be set by the user), or Crevasse splay or levees (fluviatil or turbiditic). Each of these associated/related formations may have their own rules regarding the meshing of these formations (for instance, in FIG. 6c, the size of the cells in point bar zones 602 or in the levee zone 603.

Thanks to this method, it is possible to adequately mesh the model according to the needs and to the specific shape of the formations. If a meshing was performed prior to any formation determination, it is apparent that this meshing cannot fit the need of the modeling.

In addition the shape of other geological formations may be determined based on a distance to a previously determined formation or/and to a probability of existence of a surface of said other geological formations (function, for instance, of a distance (e.g. radial or lateral) to previously determined formations).

Figure 7A:
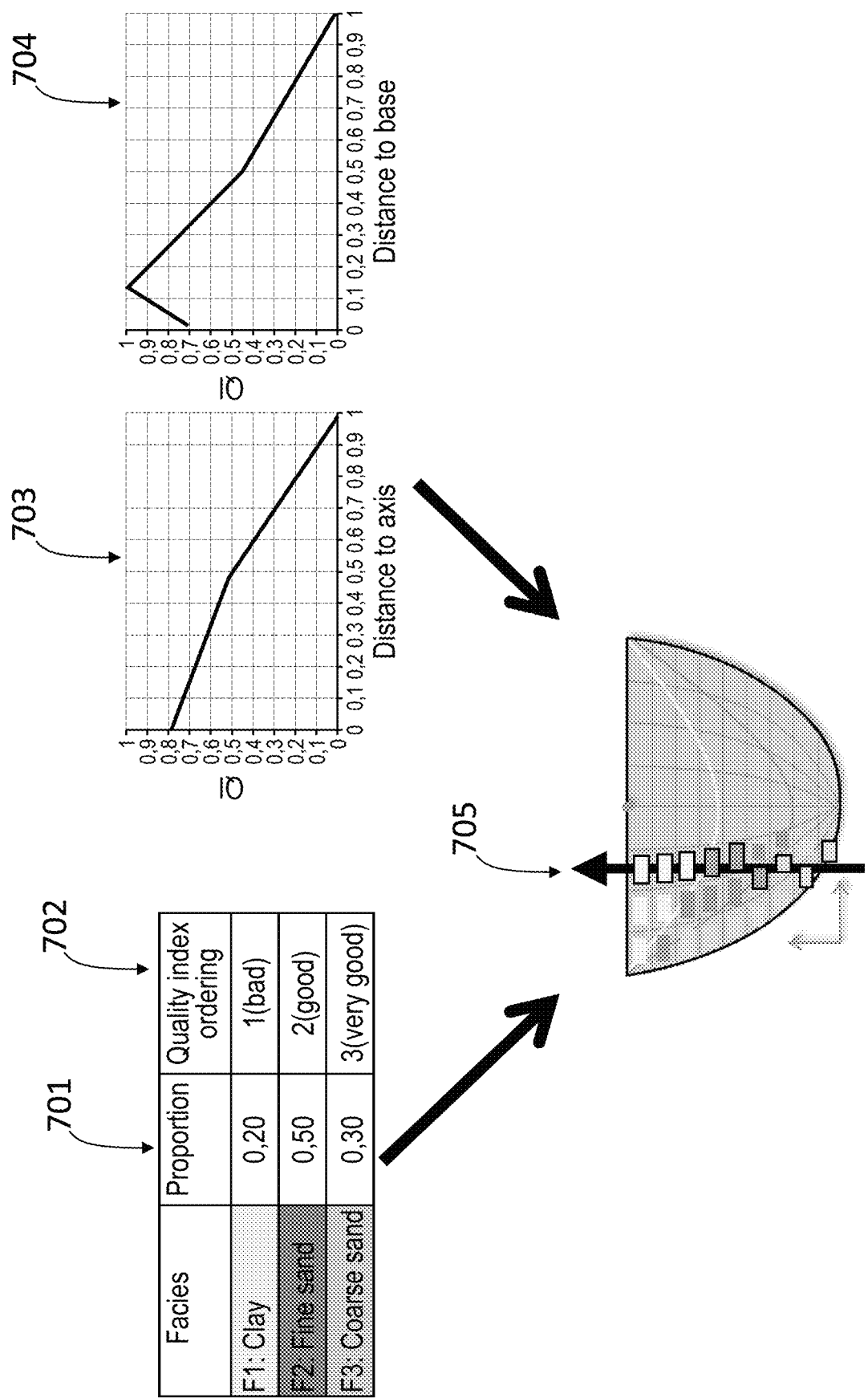
FIG. 7a exemplifies a possible process for associating a facies to a cell of a geological formation.

It is also possible to associate a facies (step 104 of FIG. 1) to each cell of the newly created mesh (i.e. for each geological formation) as shown in FIG. 7a.

This association may be based on:
quality index distributions $QI_i(p)$ for each driver i function of the considered (absolute or relative) position p (element 703 and 704 being respectively the facies quality index distribution function of the distance to the vertical axis 201-306 of the shape of the bed and the facies quality index distribution function of the distance to the base 306 of the bed),
facies proportions (column 701)
or on facies quality index ordering (column 702).

In this example of FIG. 7a, the quality index distributions are function of the distance to the vertical axis 201-306 of the shape of the bed and of the distance to the base 306 of the bed, but other geological formations may have quality index distributions function of other parameters set by the operator (i.e. the person setting the modeling).

For each cell of the geological formation that is considered, said cell having a position p, a cell quality index $QI_c$ is computed as being $$QI_c = \frac{\sum_i QI_i(p)}{N}$$

(i being the current driver, N being the total number of drivers).

Then, the following process (see 705) may be used for associating a facies to a cell in a formation (having a plurality of cells):

/a/ selecting a cell with the lowest $QI_c$ within the cells in the plurality of cells having no facies associated to;
/b/ associating, to said cell, the facies with the lowest Quality index ordering (column 702) within the facies for which the proportion is not reached (column 701)
/c/ reiterating step /a/ to /c/ until all cells in the plurality of cells are associated with a facies.

It is apparent that the "lowest" words may be replaced by the "biggest" in said process.

It is also possible to associate a geological property (e.g. permeability, porosity, etc.) (step 104 of FIG. 1) to each cell of the newly created mesh (i.e. for each geological formation) as shown in FIG. 7b.

This association may be based on property quality index distributions $QI_i(p)$ for each driver i function of the considered (absolute or relative) position p (element 713 and 714 being respectively the property quality index distribution function of the distance to the vertical axis 201-306 of the shape of the bed and the property quality index distribution function of the distance to the base 306 of the bed) and on property distribution (curve 711).

Figure 7B:
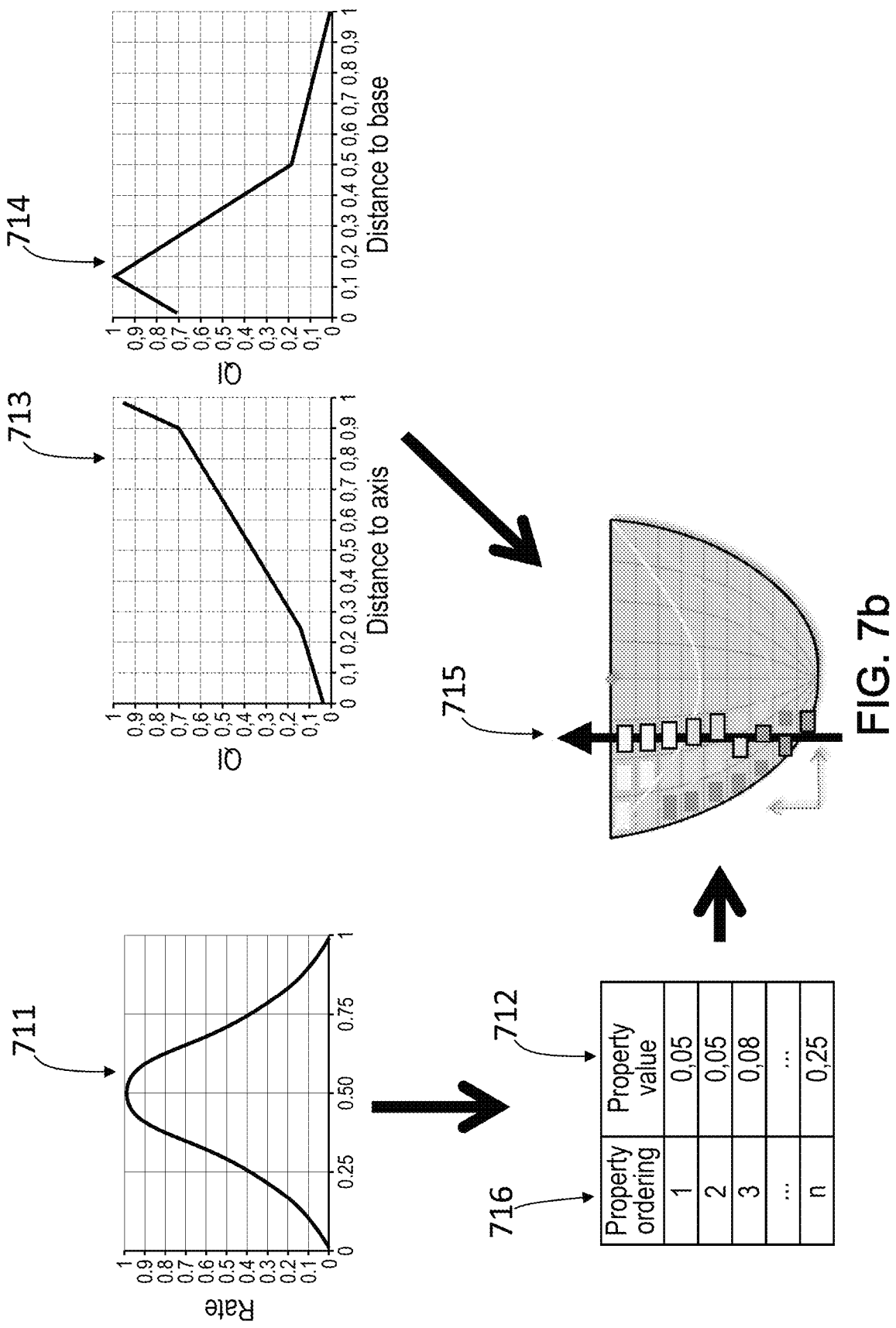
FIG. 7b exemplifies a possible process for associating a property to a cell of a geological formation.

In this example of FIG. 7b, the property quality index distributions are function of the distance to the vertical axis 201-306 of the shape of the bed and of the distance to the base 306 of the bed but other geological formations may have property quality index distributions function of other parameters set by the operator (i.e. the person setting the modeling).

For each cell of the geological formation that is considered, said cell having a position p, a cell quality index $QI_c$ is computed as being $$QI_{ce} = \frac{\sum_i QI_i(p)}{N}$$

(i being the current driver, N being the total number of drivers).

Then, the following process (see 715) may be used for associating a property to a cell in a formation (having a plurality of cells):

/a/ determining M random draw of property values in the property distribution 711 (M being the number of cells in the plurality of cells) and ordering said M random draw from the lowest to the greatest value (see 712) (the index/rank/order of the random draw for this ordering is the "property ordering"));
/b/ selecting a cell with the lowest $QI_c$ within the cells in the plurality of cells having no property associated to;
/c/ associating, to said cell, the random draw (property) with the lowest property ordering (column 716) within the random draws that have not been associated yet with a cell (column 712)
/d/ reiterating steps /a/ to /d/ until all cells in the plurality of cells are associated with a property.

It is apparent that the "lowest" (respectively "biggest") words may be replaced by the "biggest" (respectively "lowest") in said process.

For part(s) of the model that is/are not determined geological formations (i.e. background zone), it is possible to mesh (step 105 of FIG. 1) it/them with common method(s)

and to associate its/their cells with property/facies (step 106 of FIG. 1) according to the relative position of the cells in regard of the geological formation determined (e.g. facies probabilities may be set by the operator according to a radial/lateral distance of a determined geological formation).

Figure 8:
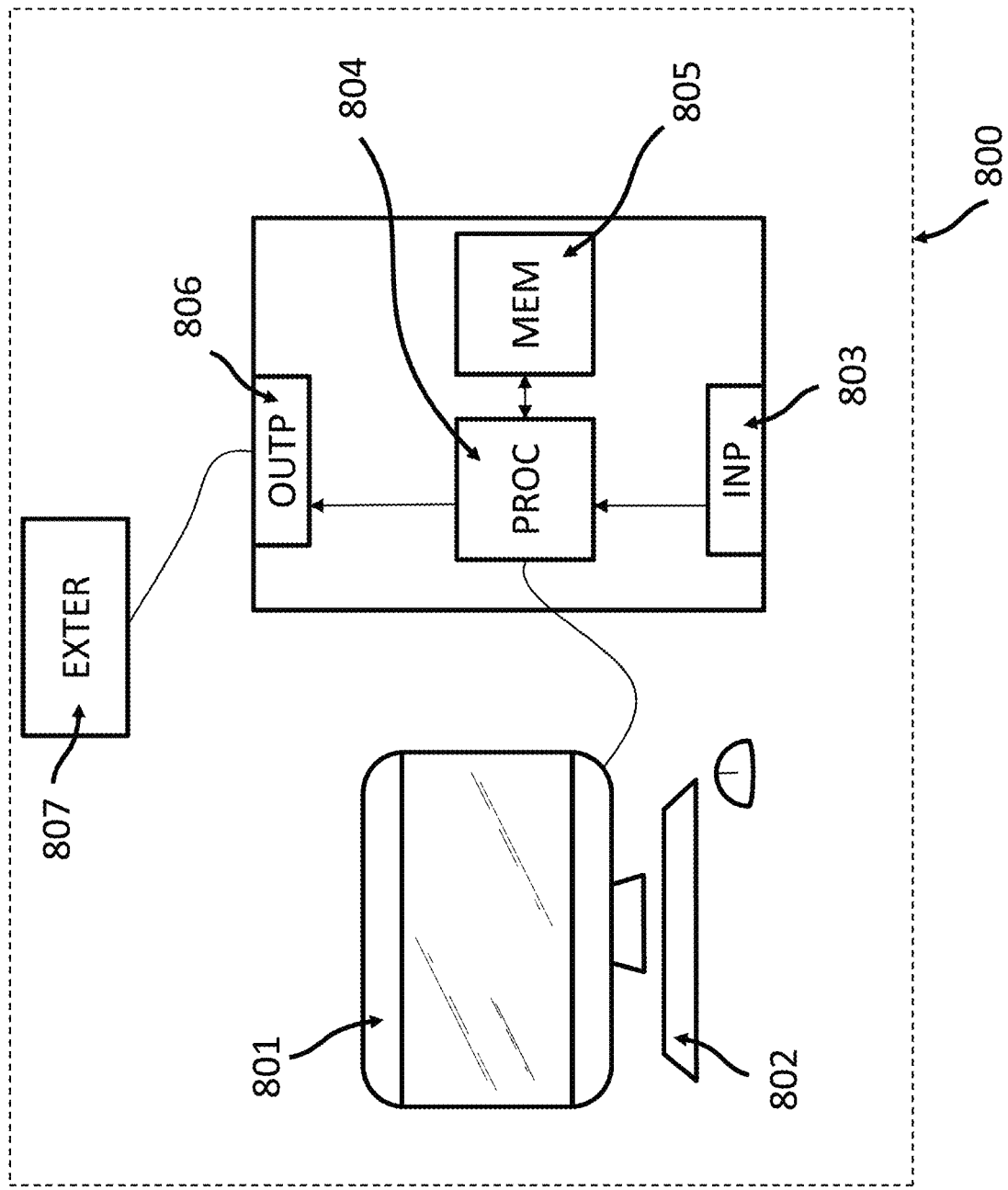
FIG. 8 is a possible embodiment for a device that enables the present invention.

FIG. 8 is a possible embodiment for a device that enables the present invention.

In this embodiment, the device 800 comprise a computer, this computer comprising a memory 805 to store program instructions loadable into a circuit and adapted to cause circuit 804 to carry out the steps of the present invention when the program instructions are run by the circuit 804.

The memory 805 may also store data and useful information for carrying the steps of the present invention as described above.

The circuit 804 may be for instance:
- a processor or a processing unit adapted to interpret instructions in a computer language, the processor or the processing unit may comprise, may be associated with or be attached to a memory comprising the instructions, or
- the association of a processor/processing unit and a memory, the processor or the processing unit adapted to interpret instructions in a computer language, the memory comprising said instructions, or
- an electronic card wherein the steps of the invention are described within silicon, or
- a programmable electronic chip such as a FPGA chip (for «Field-Programmable Gate Array»).

This computer comprises an input interface 803 for the reception of data/model/input used for the above method according to the invention and an output interface 806 for providing a complete model.

To ease the interaction with the computer, a screen 801 and a keyboard 802 may be provided and connected to the computer circuit 804.

Expressions such as "comprise", "include", "incorporate", "contain", "is" and "have" are to be construed in a non-exclusive manner when interpreting the description and its associated claims, namely construed to allow for other items or components which are not explicitly defined also to be present. Reference to the singular is also to be construed in be a reference to the plural and vice versa.

A person skilled in the art will readily appreciate that various parameters disclosed in the description may be modified and that various embodiments disclosed may be combined without departing from the scope of the invention.

The invention claimed is:

1. A computer-implemented method enabling industrial extraction of hydrocarbons from a hydrocarbon reservoir, comprising:
    receiving, by an input interface of a computer, an unmeshed model representing real subsoil forming the hydrocarbon reservoir;
    determining a sediment trajectory in said model, wherein determining the sediment trajectory comprises determining a displacement of particles in said model by superimposing:
        a deterministic term that is defined based on observed data with respect to the real subsoil, and
        a stochastic term parametrized at least by the observed data, the stochastic term comprising a superposition of a meandriform term and a random perturbation;
    based on the sediment trajectory, determining at least one parametric surface describing a sediment formation in said model; and
    based on the least one parametric surface, meshing the sediment formation in said model;
    wherein the method further comprises:
        determining at least one associated surface as a function of the at least one parametric surface, said associated surface describing an associated geological formation associated with the sediment formation, wherein the associated geological formation has rules of meshing independent of rules of meshing of the sediment formation;
        based on said at least one associated surface, meshing the associated geological formation;
        determining a composition of the real subsoil based on the meshed sediment formation and the meshed associated geological formation;
        outputting, by an output interface of a computer, a complete model representing the composition of the real subsoil; and
        locating, at a location in the real subsoil, a well for extraction of hydrocarbons from the hydrocarbon reservoir, wherein the well is located based on the composition of the real subsoil.

2. The method according to claim 1, wherein determining the at least one parametric surface is based on a Non-Uniform Rational B-Splines (NURBS) curve or a NURBS surface or a NURBS volume.

3. The method according to claim 1, wherein the sediment trajectory is determined based on a stochastic process.

4. The method according to claim 1, wherein the sediment formation is meshed using at least one method of a group comprising a Quadtree meshing method, Octree meshing method, Front method, Delaunay method, Prograding grid, divergent grid, and aggrading grid.

5. The method according to claim 1, wherein the method further comprises:
    meshing of at least a part of the model that is not a determined formation.

6. A non-transitory computer readable storage medium, having stored thereon a computer program comprising program instructions, the computer program being loadable into a data-processing device and adapted to cause the data-processing device to carry out the steps of the method according to claim 1 when the computer program is run by the data-processing device.

7. A computing device enabling industrial extraction of hydrocarbons from a hydrocarbon reservoir, comprising:
    a computer interface configured to receive an unmeshed model representing real subsoil;
    a circuit configured to determine a sediment trajectory in said model, wherein said circuit is configured to determine the sediment trajectory by determining a displacement of particles in said model by superimposing:
        a deterministic term that is defined based on observed data with respect to the real subsoil, and
        a stochastic term parametrized at least by the observed data, the stochastic term comprising a superposition of a meandriform term and a random perturbation;
    a circuit configured to determine, based on the sediment trajectory, at least one parametric surface describing a sediment formation in said model; and
    a circuit configured to mesh, based on the least one parametric surface, the sediment formation in said model to produce a meshed sediment formation;
    wherein the computing device further comprises:
        a circuit configured to determine at least one associated surface as a function of the at least one parametric surface, said associated surface describing an associated geological formation associated with the sediment formation, wherein the associated geological formation has rules of meshing independent of rules of meshing of the sediment formation;
a circuit configured to mesh the associated geological formation, based on said at least one associated surface, to produce a meshed associated geological formation;
a circuit configured to determine a composition of the real subsoil for use in hydrocarbon industries, based on the meshed sediment formation and the meshed associated geological formation; and
an output interface configured to output:
  a complete model representing the composition of the real subsoil, and
  a location of a well in the real subsoil for extraction of hydrocarbons from the hydrocarbon reservoir, wherein the well is located based on the composition of the real subsoil.

* * * * *